United States Patent
Cabri et al.

(10) Patent No.: US 11,078,231 B2
(45) Date of Patent: Aug. 3, 2021

(54) PROCESS FOR PURIFICATION OF CARFILZOMIB INTERMEDIATE

(71) Applicant: FRESENIUS KABI ONCOLOGY LIMITED, New Delhi (IN)

(72) Inventors: Walter Cabri, Milan (IT); Saswata Lahiri, Haryana Gurugram (IN); Govind Singh, Haryana Gurugram (IN); Sarbjot Singh Sokhi, Haryana Gurugram (IN); Maneesh Kumar Pandey, Haryana Gurugram (IN); Raj Narayan Tiwari, Haryana Gurugram (IN); Sonu Prasad Shukla, Haryana Gurugram (IN)

(73) Assignee: FRESENIUS KABI ONCOLOGY LTD, New Delhi (IN)

( * ) Notice: Subject to any disclaimer, the term of this patent is extended or adjusted under 35 U.S.C. 154(b) by 0 days.

(21) Appl. No.: 16/332,717

(22) PCT Filed: Sep. 13, 2017

(86) PCT No.: PCT/IB2017/055517
§ 371 (c)(1),
(2) Date: Mar. 12, 2019

(87) PCT Pub. No.: WO2018/051237
PCT Pub. Date: Mar. 22, 2018

(65) Prior Publication Data
US 2019/0218249 A1 Jul. 18, 2019

(30) Foreign Application Priority Data
Sep. 14, 2016 (IN) .............................. 201611031297

(51) Int. Cl.
| | |
|---|---|
| *A61K 38/00* | (2006.01) |
| *C07K 1/22* | (2006.01) |
| *C07D 303/32* | (2006.01) |
| *C07C 53/18* | (2006.01) |
| *C07K 5/107* | (2006.01) |
| *C07K 5/087* | (2006.01) |
| *C07K 5/103* | (2006.01) |
| *A61P 35/00* | (2006.01) |

(52) U.S. Cl.
CPC ................ *C07K 1/22* (2013.01); *C07C 53/18* (2013.01); *C07D 303/32* (2013.01); *C07K 5/0812* (2013.01); *C07K 5/1008* (2013.01); *C07K 5/1016* (2013.01); *A61K 38/00* (2013.01); *A61P 35/00* (2018.01); *C07B 2200/13* (2013.01)

(58) Field of Classification Search
CPC combination set(s) only.
See application file for complete search history.

(56) References Cited

U.S. PATENT DOCUMENTS

| | | | |
|---|---|---|---|
| 7,231,818 | B2 | 6/2007 | Sheng et al. |
| 7,417,042 | B2 | 8/2008 | Smyth et al. |
| 8,207,297 | B2 | 6/2012 | Smyth et al. |
| 2016/0115198 | A1 | 4/2016 | Kovi et al. |

FOREIGN PATENT DOCUMENTS

| | | |
|---|---|---|
| WO | WO 2005/105827 A2 | 11/2005 |
| WO | WO 2014/018807 A1 | 1/2014 |
| WO | WO 2016/088031 A1 | 6/2016 |
| WO | WO 2016/108204 A1 | 7/2016 |

OTHER PUBLICATIONS

Greene et al., "Protective Groups in Organic Synthesis," 3rd Ed., pp. 17-245, J. Wiley & Sons (1999).
Screen et al., "Nature of Pharmacophore Influences Active Site Specificity of Proteasome Inhibitors," *Journal of Biological Chemistry* 285(51): 40125-40134 (2010).
Screen et al., "Synthesis and analytical data for compounds," (2010) http://www.jbc.org/content/suppl/2010/10/08/M110.160606.DC1/jbc.M110.160606-1.pdf.
European Patent Office, International Search Report in International Application PCT/IB2017/055517 (dated Nov. 29, 2017).
European Patent Office, Written Opinion in International Application PCT/IB2017/055517 (dated Nov. 29, 2017).
International Bureau of WIPO, International Preliminary Report on Patentability in International Application PCT/IB2017/055517 (dated Mar. 19, 2019).

*Primary Examiner* — Thomas S Heard
(74) *Attorney, Agent, or Firm* — Leydig, Voit & Mayer, Ltd.

(57) ABSTRACT

The present invention relates to a process for the purification of compound of formula II, wherein X may be independently selected from trifluoroacetic acid, hydrochloric acid, hydrobromic acid, p-toluene sulfonic acid and phosphoric acid; its isolation as solid and use for the preparation of carfilzomib.

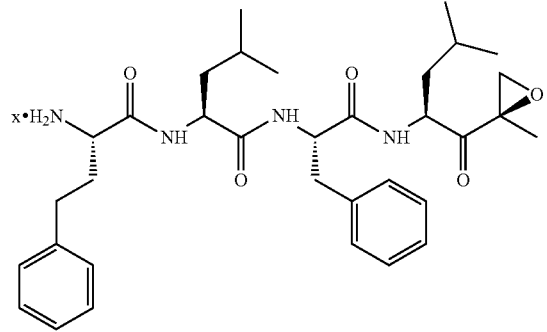

Formula II

13 Claims, 1 Drawing Sheet

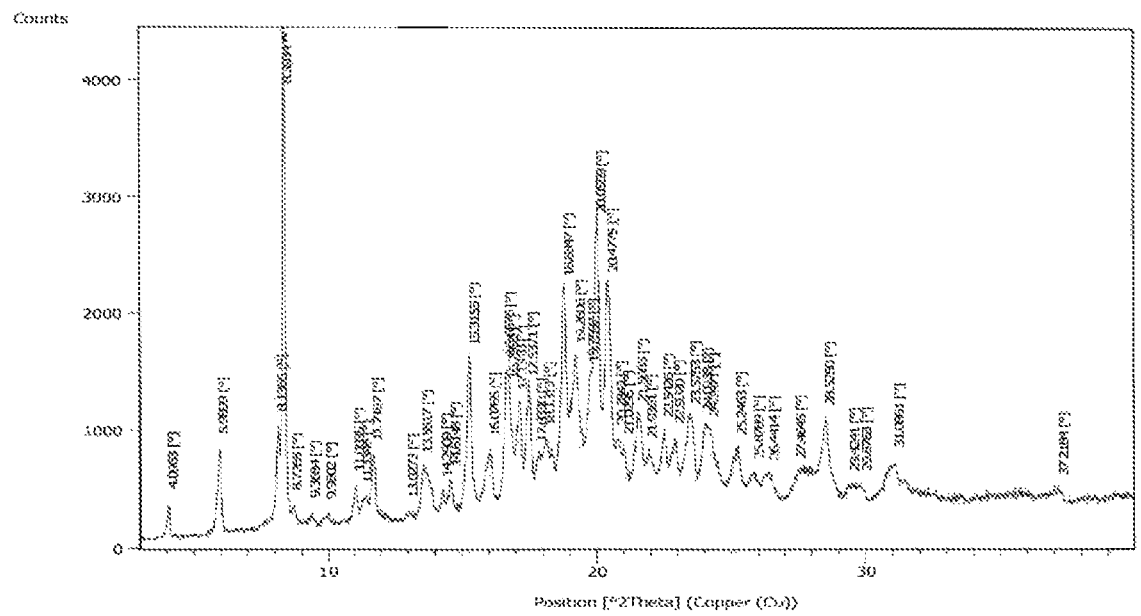

PROCESS FOR PURIFICATION OF CARFILZOMIB INTERMEDIATE

CROSS-REFERENCE TO RELATED APPLICATIONS

This patent application is the U.S. national phase of International Application No. PCT/IB2017/055517, filed on Sep. 13, 2017, which claims the benefit of Indian Patent Application No. IN201611031297, filed Sep. 14, 2016, the disclosures of which are incorporated herein by reference in their entireties for all purposes.

FIELD OF THE INVENTION

The present invention relates to a process for purifying an intermediate in the synthesis of carfilzomib, i.e. the compound of formula II, Formula II

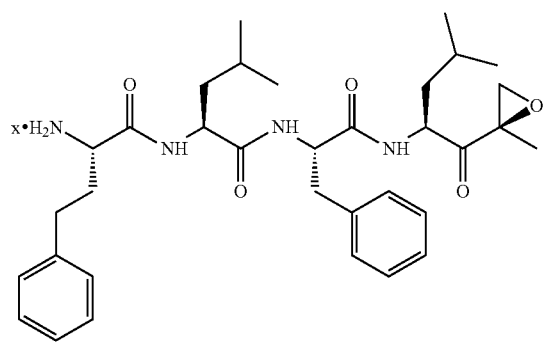

wherein X may be independently selected from trifluoroacetic acid, hydrochloric acid, hydrobromic acid, p-toluene sulfonic acid and phosphoric acid, in particular reducing the level of an impurity of formula III generally formed and/or present during synthesis of the compound of formula II, Formula III

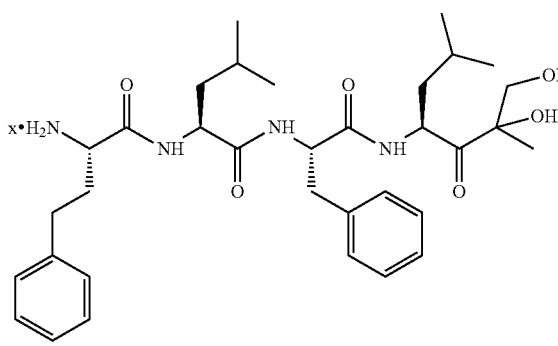

wherein X may be independently selected from trifluoroacetic acid, hydrochloric acid, hydrobrominc acid, p-toluene sulfonic acid and phosphoric acid.

The present invention also relates to the isolation of a compound of formula II as solid, preferably the compound of formula IIa and its use for the preparation of carfilzomib. The present invention further relates to a crystalline compound of formula IIa having X-ray diffraction peak at 8.39, 15.31, 17.13, 18.83, 20.05 and 20.47±0.2 degrees two-theta.

Formula IIa

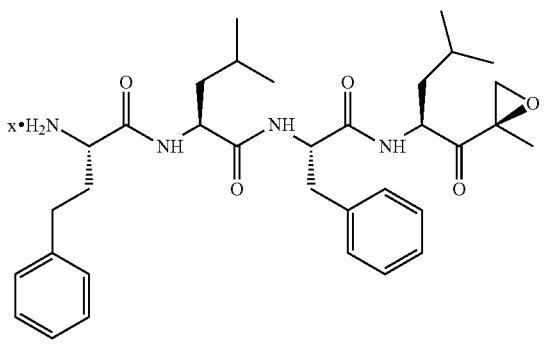

wherein X is trifluoroacetic acid

BACKGROUND OF THE INVENTION

Carfilzomib, (2S)—N-{(1S)-1-benzyl-2-[((1S)-3-methyl-1-{[(2R)-2-methyloxiran-2-yl]carbonyl}butyl)amino]-2-oxoethyl}-4-methyl-2-({(2S)-2-[(morpholin-4-ylacetyl)amino]-4-phenylbutanoyl}amino)pentanamide, is represented by the formula I:

Formula I

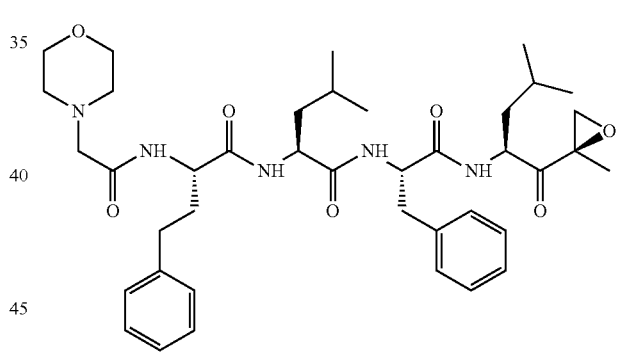

Carfilzomib (CFZ, marketed under the trade name Kyprolis, Onyx Pharmaceuticals, Inc.) is a tetrapeptide epoxyketone and a selective proteasome inhibitor. It is an analog of epoxomicin. It was approved by the U.S. Food and Drug Administration (FDA) for use in combination with dexamethasone or with lenalidomide plus dexamethasone in patients with relapsed or refractory multiple myeloma, who have received one to three lines of therapy. It is also indicated as a single agent for the treatment of patients with relapsed or refractory multiple myeloma, who have received one or more lines of therapy.

Carfilzomib as represented by formula I is disclosed in U.S. Pat. No. 7,417,042. The synthetic scheme described in U.S. Pat. No. 7,417,042 is depicted below as scheme-1:

Scheme -1
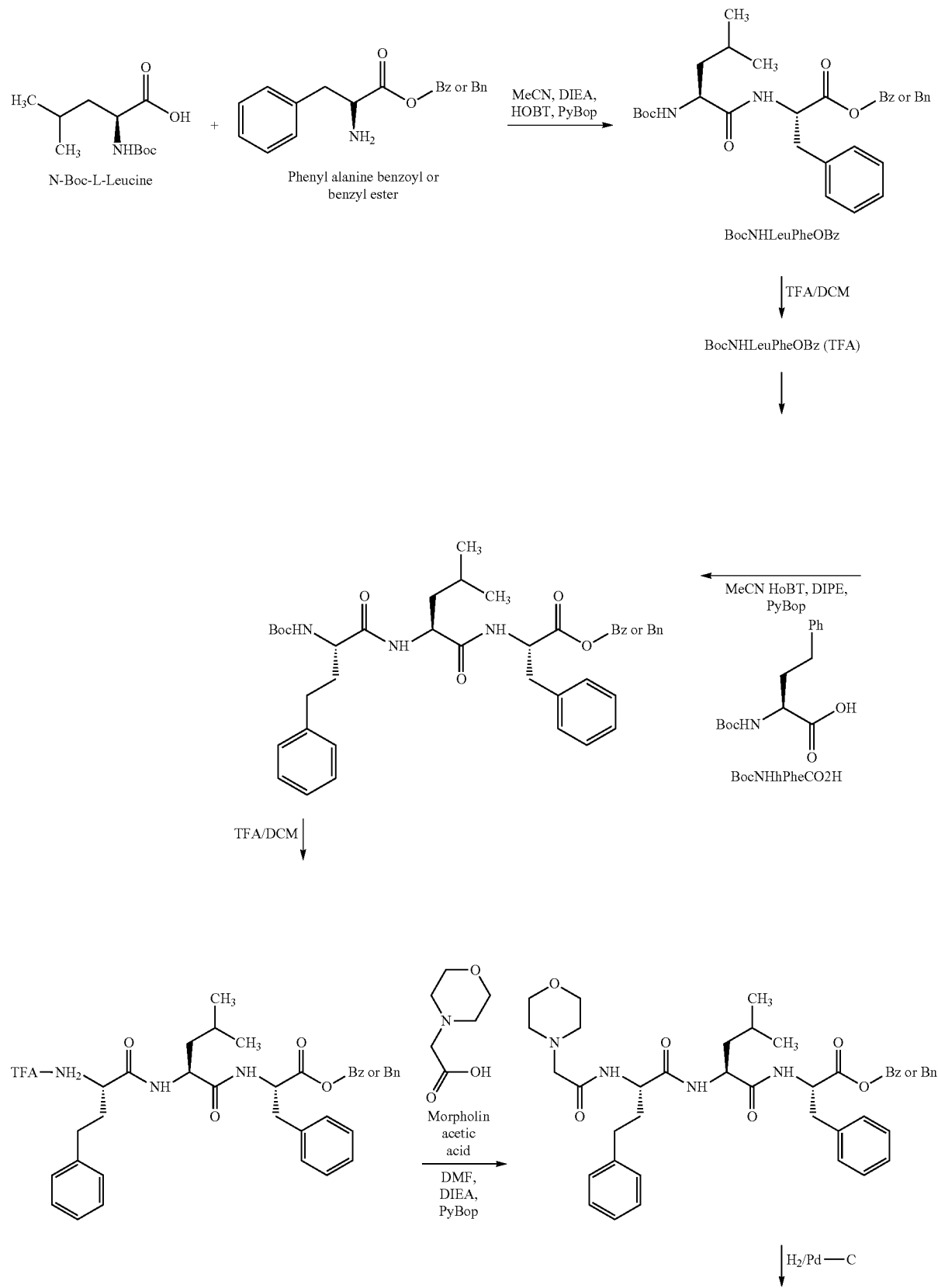

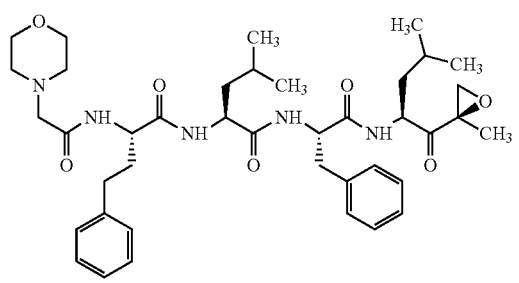

I
CARFILZOMIB

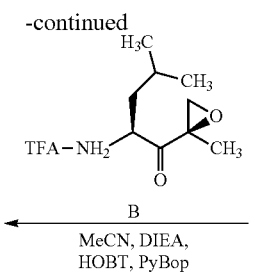

B

MeCN, DIEA,
HOBT, PyBop

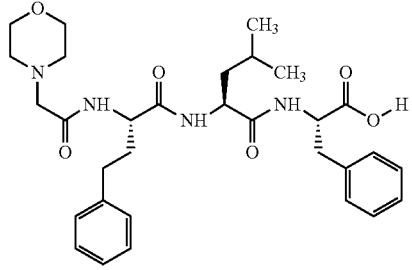

wherein, "Boc" means tert-butoxycarbonyl; Bz and Bn means benzoyl and benzyl groups respectively; MeCN means acetonitrile; TFA means trifluoroacetic acid; DMF means dimethyl formamide; DCM means Dichloromethane; DIEA means diisopropyl ethyl amine; HOBT means hydroxyl benzotriazole; PyBop means benzotriazol-1-yl-oxytripyrrolidinophosphonium hexafluorophosphate.

Further, U.S. Pat. Nos. 7,231,818 and 8,207,297 also describe a similar process for the synthesis of carfilzomib. The inventors of the present invention found that the above mentioned scheme results in carfilzomib containing a diol carfilzomib impurity, represented herein below:

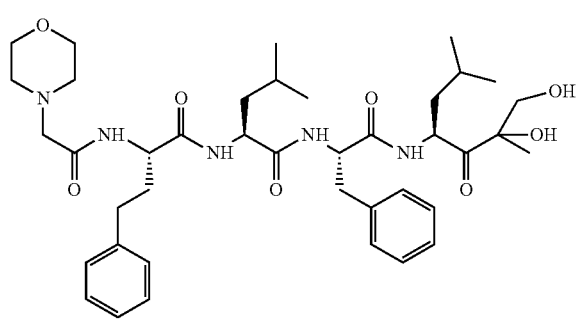

Diol Carfilzomib

A possible reason for impurity formation appears to be opening of the sensitive epoxide ring.

The removal of diol carfilzomib impurity requires multiple purifications which in turn reduces overall yield. The multiple purifications may also lead to opening of the sensitive epoxide ring.

WO2005/105827A2 discloses a process for the deprotection of a compound of formula IVa, represented herein below:

Formula IVa

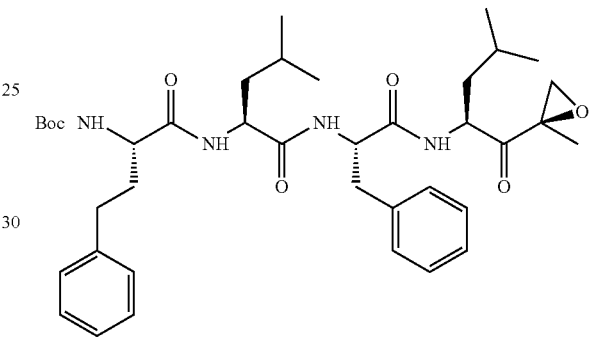

Boc: tert-butoxycarbonyl wherein Boc is tert-butoxycarbonyl. The compound of Formula IVa corresponds to Compound (CC) of WO2005/105827A2.

In WO2005/105827A2, the compound of formula IVa is treated with trifluoroacetic acid in dichloromethane for one hour at room temperature. The resulting mixture was concentrated and placed under vacuum for two hours.

The inventors of the present invention found that the above mentioned process results in the formation of an impurity of formula IIIa, represented herein below:

Formula IIIa

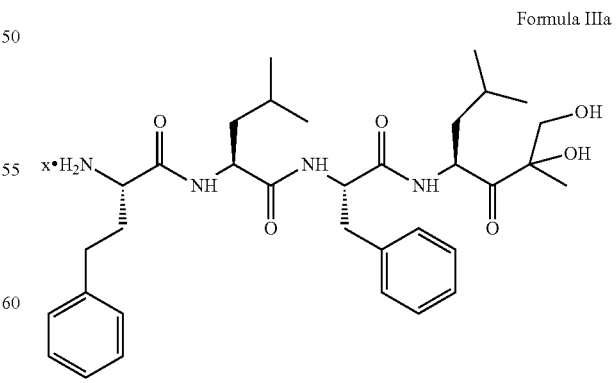

wherein X is trifluoroacetic acid

The above mentioned impurity was measured by High Performance Liquid Chromatography (HPLC) as 5.33 area % after completion of the process disclosed in WO2005/ 105827A2. It was further found that aforesaid process results in a product in oily form, which is difficult to isolate or purify.

A similar process for the synthesis of compound of formula IIa is disclosed in WO2014/018807A1. In WO2014/ 018807A1, a compound of formula IVa is treated with trifluoroacetic acid in dichloromethane for four hours at room temperature. After deprotection, the reaction mixture was concentrated to obtain the compound of formula IIa. The compounds of Formulae IVa and IIa correspond to Compounds 1068 and 1069, respectively, of WO2014/ 018807A1. The authors of WO2014/018807A1 disclose that the compound obtained by following the above process is obtained as brown oil.

The inventors of the present invention found that the compound obtained by following the process disclosed in WO2014/018807A1 contains an impurity of formula IIIa 3.06% as measured by HPLC.

Generally, impurities in an active pharmaceutical ingredient (API) may arise from degradation of the API itself, or may be a process generated impurity. The inventors of the present invention found that in the present case, the diol carfilzomib impurity is either formed due to epoxide ring opening of carfilzomib at the final stage of the preparation of carfilzomib or content of open epoxide ring present (or forms) in intermediates of carfilzomib may carry forward along with intermediates to form the diol carfilzomib impurity.

The removal of diol carfilzomib impurity is very difficult and even by using different purification methods including recrystallization, the impurity remains in the final compound in an undesired amount.

The multiple purifications of carfilzomib are also not desirable due to the presence of the sensitive epoxide ring, which may open during purification to form the diol carfilzomib impurity. Hence, there is a need to control the diol impurity of formula III at the intermediate stage of the preparation of carfilzomib to prepare carfilzomib free from the diol carfilzomib impurity.

The inventors of the present application have found a process of purification of compound of formula II to prepare a substantially pure compound of formula II. In particular, the compound of formula II contains less than 0.05 area-% HPLC of impurity of formula III.

SUMMARY OF THE INVENTION

In a first aspect, the present invention relates to a process for purification of the compound of formula II, Formula II

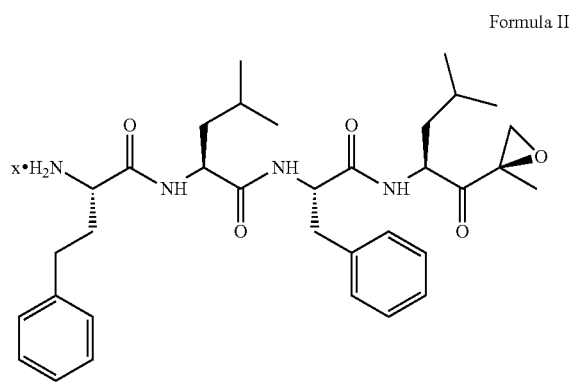

wherein X may be independently selected from trifluoroacetic acid, hydrochloric acid, hydrobrominc acid, p-toluene sulfonic acid and phosphoric acid,
comprising the steps of:
i) treating the compound of formula II, preferably the compound of formula IIa with an alkali metal perhalate in a suitable solvent;
ii) adding anti-solvent; and
iii) isolating the substantially pure compound of formula II or IIa.

Another aspect of the present invention relates to a crystalline compound of formula IIa.

Another aspect of the present invention relates to a process comprising converting the substantially pure compound of formula II or IIa into carfilzomib.

A further aspect of the present invention relates to carfilzomib containing less than 0.15 area-% of diol carfilzomib impurity as measured by high performance liquid chromatography (HPLC).

BRIEF DESCRIPTION OF THE DRAWINGS

The figure is an illustration of a PXRD pattern of a crystalline compound of formula IIa.

DETAILED DESCRIPTION OF THE INVENTION

Definitions

The following definitions are used in connection with the present application unless the context indicates otherwise.

The term "amine protecting group" as used herein refers to a group that blocks (i.e., protects) the amine functionality while reactions are carried out on other functional groups or parts of the molecule. Those skilled in the art will be familiar with the selection, attachment, and cleavage of amine protecting groups and will appreciate that many different protective groups are known in the art, the suitability of one protective group or another being dependent on the particular synthetic scheme planned. Treatises on the subject are available for consultation, such as Greene and Wuts, "Protective Groups in Organic Synthesis," 3rd Ed., pp. 17-245 (J. Wiley & Sons, 1999), the disclosure of which is incorporated herein by reference.

The term alkali metal refers exclusively to lithium (Li), sodium (Na) and potassium (K).

Alkali metal perhalate refers to lithium periodate, sodium periodate, potassium periodate, lithium perbromate, sodium perbromate, potassium perbromate, lithium perchlorate, sodium perchlorate and potassium perchlorate.

Preferably, the invention provides carfilzomib free from the diol impurity. The term 'carfilzomib free from the diol carfilzomib impurity_ refers to carfilzomib containing a diol carfilzomib impurity of less than 0.15 area-% as measured by high performance liquid chromatography (HPLC). More preferably, carfilzomib, as disclosed herein, contains a diol carfilzomib impurity of less than 0.10 area-% as measured by HPLC and most preferably contains a diol carfilzomib impurity of less than 0.05 area-% as measured by HPLC.

The term 'substantially pure compound of formula II_ refers to compound of formula II containing an impurity of formula III of less than 0.15 area % as measured by HPLC. More preferably, the compound of formula II, as disclosed herein, contains an impurity of formula III of less than 0.10 area % as measured by HPLC and most preferably contains an impurity of formula III of less than 0.05 area % as measured by HPLC.

The term:X˜ of compound of formula II or compound of formula III relates to corresponding salts selected from the group comprising of trifluoroacetic acid, hydrochloric acid, hydrobromic acid, phosphoric acid and para toluenesulphonic acid. The term:X˜ resembles with the choice of deproctecting acids used for deproctection of $PG_1$ protecting groups of compound of formula IV, represented herein below:

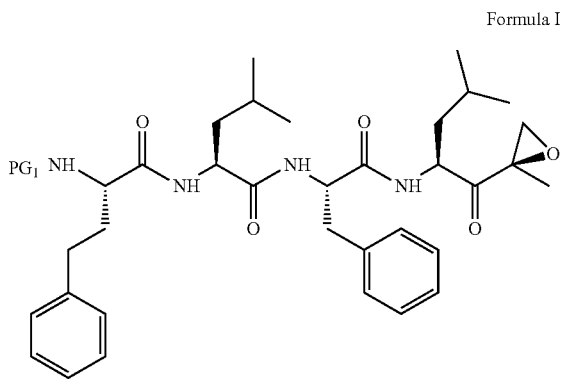

Formula IV $PG_1$: tert-butoxycarbonyl (BOC), fluorenylmethyloxycarbonyl (FMOC), triphenlmethyl (Trityl), methanesulfonyl (Mesyl) or acyl wherein $PG_1$ may be independently selected from tert-butoxycarbonyl (BOC), fluorenylmethyloxycarbonyl (FMOC), triphenylmethyl (Trityl), methanesulfonyl (Mesyl) and acyl.

The terms 'about, general, generally_ and the like are to be construed as modifying a term or value such that it is not an absolute. Such terms will be defined by the circumstances and the terms that they modify, as those terms are understood by those skilled in the art. This includes, at very least, the degree of expected experimental error, technique error and instrument error for a given technique used to measure a value.

As used herein, the terms 'comprising_ and 'comprises_ mean the elements recited, or their equivalents in structure or function, plus any other element or elements which are not recited.

The terms 'having_ and 'including_ are also to be construed as open ended. All ranges recited herein include the endpoints, including those that recite a range between two values. Whether so indicated or not, all values recited herein are approximate as defined by the circumstances, including the degree of expected experimental error, technique error, and instrument error for a given technique used to measure a value.

The term 'optional_ or 'optionally_ is taken to mean that the event or circumstance described in the specification may or may not occur, and that the description includes instances where the event occurs and instances where it does not.

The term 'anti-solvent_ refers to a liquid that, when combined with a solution of compound of formula II, reduces solubility of the compound of formula II in the solution, causing crystallization or precipitation in some instances spontaneously, and in other instances with additional steps, such as seeding, cooling, scratching, and/or concentrating.

In a first aspect, the application provides a process for purification of a compound of formula II,

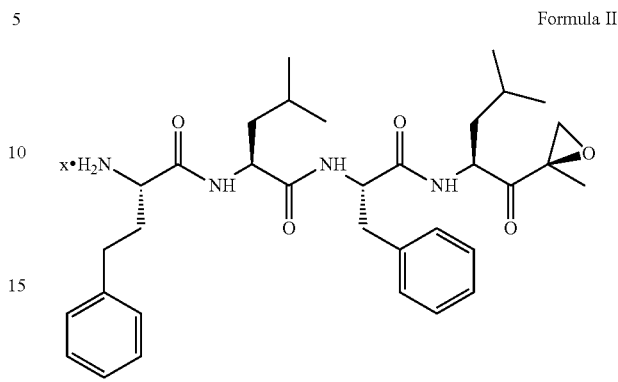

Formula II wherein X may be independently selected from trifluoroacetic acid, hydrochloric acid, hydrobrominc acid, p-toluene sulfonic acid and phosphoric acid by treating it with an alkali metal perhalate in a suitable solvent followed by addition of anti-solvent to isolate a substantially pure compound of formula II containing an impurity of formula III in an amount of less than 0.10 area-% as measured by high performance liquid chromatography (HPLC).

The alkali metal perhalate may be selected from the group consisting of lithium periodate, sodium periodate, potassium periodate, lithium perbromate, sodium perbromate, potassium perbromate, lithium perchlorate, sodium perchlorate and potassium perchlorate. Preferably, the alkali metal perhalate is an aqueous solution of sodium periodate.

The inventors of the present invention found that the use of alkali metal perhalate reduces the level of the impurity of formula III in the compound of formula II significantly. In particular, the formula III impurity is reduced to less than 0.05 area % HPLC.

The inventors also found that other oxidizing agents such as perchloric acid ($HClO_4$) may also reduce the formula III impurity effectively.

At this stage, the monitoring of formula III impurity is very advantageous as it reduces the amount of formation of diol carfilzomib. Alternatively, it also avoids the multiple purifications of carfilzomib to remove the diol carfilzomib.

The compound of formula II is formed due to deprotection of compound of formula IV, the formation of corresponding salts depend on the use of corresponding acid used for the deprotection of $PG_1$ of compound of formula IV.

$PG_1$ is a suitable amine protecting group. Suitable amine function protection groups and protection and deprotection methods are well known in the art (see notably "Protective groups in organic synthesis", Greene T. W. and Wuts P. G. M., Wiley-Interscience, 1999). Preferably, the suitable amine protecting groups—PG1 can be selected from tert-butyloxycarbonyl (Boc), 9-fluorenylmethyloxycarbonyl (FMOC), triphenylmethyl (Trityl), methanesulfonyl (Mesyl) and acyl.

The amine protected compounds of formula IV are converted to the corresponding salt of the compounds of formula II by cleaving off the protecting group $PG_1$ using standard conditions for the deprotection of amines, preferably a suitable acid such as trifluoroacetic acid, hydrochloric acid, hydrobromic acid, phosphoric acid and para toluene-sulphonic acid can be used in a suitable solvent such as tetrahydrofuran, ethyl acetate, dichloromethane and acetonitrile for the deprotection of amines.

The amine deprotection may be carried out using from 1 to 10 equivalents of acid, more preferably from 1 to 2 equivalents at reduced or elevated temperatures, for example from −30° C. to 40° C., more preferably from −10° C. to 10° C., over a time period ranging from 1 minute to 10 hours, more preferably from 30 minutes to 5 hours. It is advantageous to perform the deprotection reaction at low temperature preferably below 0° C. The deprotection at low temperature has significantly reduced the opening of sensitive epoxide ring of compound of formula II which in turn is useful in reducing the formation of formula III impurity. The low temperature condition is useful but it does not completely avoid the formation of formula III impurity.

In a preferred embodiment, the compound of formula II, wherein X is trifluoroacetic acid is prepared by treating a compound of formula IVa with trifluoroacetic acid optionally in the presence of a suitable solvent such as dichloromethane. The reaction mixture is stirred for 1 to 10 hours, more preferably for 2 to 8 hours at −5° C. to 0° C.

The compound of formula II can be isolated as solid or it can be used without isolation for the next step of purification with an alkali metal perhalate. Preferably, it is isolated by using a suitable technique known in the art, such as quenching with an anti-solvent followed by precipitation or by extraction from a suitable solvent followed by removal of solvent from the reaction mixture by evaporation, distillation and the like or any other methods can be employed. The isolation of compound of formula II is preferred as it reduces the content of dissolved organic and/or inorganic impurities.

The obtained compound of formula II, generally having impurity of formula III more than 0.25 area-% HPLC, is treated with alkali metal perhalate in suitable solvent to remove the formula III impurity. The purification process is performed by stirring the reaction mixture for 2 to 15 hours, more preferably for 4 to 10 hours at a range of temperature from 5° C. to 40° C., more preferably at 20° C. to 30° C.

After purification, the isolation of substantially pure compound of formula II is carried out by addition of suitable anti-solvent. The addition of anti-solvent may be achieved either by adding the reaction mixture to the anti-solvent or by adding an anti-solvent to the reaction mixture. Addition may be slow or instant. The substantially pure compound of formula II may optionally be washed with suitable solvent and dried under suitable drying conditions.

The drying may be suitably carried out using any of an air tray dryer, vacuum tray dryer, fluidized bed dryer, spin flash dryer, flash dryer, and the like. The drying may be carried out at any suitable temperature and under atmospheric pressure or above, or under reduced pressure.

In a preferred embodiment, the substantially pure compound of formula II is crystalline.

The suitable solvent for the purification of compound of formula II may be selected from the group consisting of tetrahydrofuran, dioxane, dimethoxyethane, methanol, ethanol, propanol, isopropyl alcohol, n-butanol, ethyl acetate, acetonitrile, propionitrile, dimethylformamide, dimethylacetamide and dimethyl sulfoxide or mixtures thereof. Preferably, the solvent is tetrahydrofuran.

The suitable anti-solvent may be selected from the group consisting of water, hydrocarbon such as n-heptane, n-hexane, methyl tert-butyl ether, diisopropyl ether. Preferably, the anti-solvent is water.

The preferred alkali metal perhalate may be selected from the group consisting of alkali metal perhalate as discussed above. Most preferably, the alkali metal perhalate is sodium periodate.

The isolation of compound of formula II is not reported in the prior art procedures which makes the removal of impurities difficult; however, the purification process of the present invention involves the use of an alkali metal perhalate followed by isolation of a substantially pure compound of formula II as crystalline solid, wherein the content of the diol impurity of formula III is reduced to less than 0.05 area-% HPLC.

Preferably, the invention provides carfilzomib containing less than 0.15 area-% of diol carfilzomib impurity as measured by high performance liquid chromatography (HPLC). More preferably, the carfilzomib contains a diol carfilzomib impurity of less than 0.10 area-% as measured by HPLC and most preferably contains a diol carfilzomib impurity of less than 0.05 area-% as measured by HPLC. The carfilzomib can be crystalline or amorphous.

In an embodiment, the substantially pure compound of formula II, preferably a compound of formula IIa is further utilized for the preparation and isolation of carfilzomib using methods known in the art such as disclosed in article: Journal of Biological Chemistry Volume 285 No. 51, 40125-40134; 2010. The isolated carfilzomib preferably is free from the diol carfilzomib impurity, e.g., contains less than 0.15 area-% as measured by HPLC. More preferably, the isolated carfilzomib contains a diol carfilzomib impurity of less than 0.10 area-% as measured by HPLC and most preferably contains a diol carfilzomib impurity of less than 0.05 area-% as measured by HPLC. The isolated carfilzomib can be crystalline or amorphous.

An HPLC method which is preferably used in the context of the present invention is given in the experimental section further below.

Another aspect of the present invention provides a novel crystalline compound of formula IIa and its use for the preparation of carfilzomib.

The crystalline compound of formula IIa shows X-ray diffraction peak at an angle of refraction 2 theta (:), of 8.39, 15.31, 17.13, 18.83, 20.05 and 20.47±0.2 degrees; preferably it includes five or more peaks at angles of refraction 2 theta (:) selected from the group consisting of 4.09, 5.98, 8.13, 8.39, 8.72, 9.36, 9.98, 11.00, 11.33, 11.71, 13.02, 13.55, 14.29, 14.61, 15.31, 16.07, 16.65, 16.79, 17.13, 17.53, 17.83, 18.13, 18.83, 19.26, 19.75, 20.05, 20.47, 20.78, 21.02, 21.56, 21.93, 22.54, 22.93, 23.57, 24.02, 24.24, 25.87, 26.44, 27.46, 28.52, 29.42, 29.87, 31.08 and 37.21±0.2 degrees.

X-ray Powder Diffraction (XRPD): XRPD analysis was conducted on a Panalytical, Model-Empyrean X-Ray powder diffractometer. The instrumental parameters are mentioned below:

Start position [2 Theta]: 3.0
End position [2 Theta]: 40.0
Step size [2 Theta]: 0.013
Scan step time (s): 39.27
Anode material: Cu
Generator setting: 40 mA, 45 KV
Spinning: Yes
Goniometer: theta: theta
Sample stage: Reflection-transmission spinner
Sample mode: Reflection
Sample specimen preparation: Sample back loading technique The carfilzomib according to the invention can be used to prepare a composition, such as a pharmaceutical composition. In an embodiment, the composition comprises carfilzomib produced by a process according to the present invention and a pharmaceutically acceptable excipient. Non-limiting examples of pharmaceutically acceptable excipients include diluents, salts, buffers, pH adjusters, stabilizers, solubilizers, solvents, and preservatives. In an embodiment, the excipient is a cyclodextrin, such as hydroxypropyl-$\beta$-cyclodextrin or sulfobutylether $\beta$-cyclodextrin.

EXPERIMENTAL

Detailed experimental parameters according to the present invention are provided by the following examples, which are intended to be illustrative and not limiting of all possible embodiments of the invention.

EXAMPLES

To demonstrate the benefits of the present application, examples of the prior art were worked and indicated as reference examples.

Example-1

Step A: Preparation of Crystalline Compound of Formula IIa

The compound of formula IVa (170 g) was added in trifluoroacetic acid (720 mL) followed by dichloromethane (180 mL) was added at −5° C. The reaction was stirred for 5 hours at the same temperature. After completion of the reaction, the reaction mixture was quenched with water (5200 mL). Then reaction was filtered and washed with water (1800 mL) to obtain a solid residue (having an impurity of formula IIIa: 0.43 area-% HPLC) The resulting compound was dissolved in tetrahydrofuran (720 mL), then added a solution of sodium periodate (2.7 g $NaIO_4$ in 180 mL water) and stirred for 4 hours at 25-35° C. To the resulting stirred solution water (5220 mL) was added to give the title compound (178 g) (having an impurity of formula IIIa: 0.02 area-% HPLC).

Example-2

Step A: Preparation of Crystalline Compound of Formula IIa

The compound of formula IVa (160 g) was added in trifluoroacetic acid (640 mL) followed by dichloromethane (640 mL) was added at −5° C. The reaction was stirred for 5 hours at the same temperature. After completion of the reaction, the reaction mixture was quenched with water (4800 mL). Then reaction was filtered and washed with water (two times with 800 mL each) to obtain a solid residue (having an impurity of formula IIIa: 0.29 area-% HPLC)

The resulting compound was dissolved in tetrahydrofuran (640 mL), then added a solution of sodium periodate (1.6 g $NaIO_4$ in 160 mL water) and stirred for 4 hours at 25-35° C. To the resulting mixture water (4800 mL) was added to give the title compound (157 g) (having an impurity of formula IIIa: 0.04 area-% HPLC).

REFERENCE EXAMPLES

Reference Example 1 (Example 10 of WO2005/105827A2)

Preparation of Compound of Formula IIa

The compound of formula IVa (2 g) was added to trifluoroacetic acid dichloromethane (8 mL:2 mL) mixture at 20-25° C. The reaction was stirred for 1 hour. After stirring the reaction mixture was reduced under vacuum to give brown oil (having an impurity of formula IIIa: 5.33 area-% HPLC)

Reference Example 2 (Preparation of Compound 1069 of WO2014/018807)

Preparation of Compound of Formula IIa

The compound of formula IVa (5 g) was added in trifluoroacetic acid (15 mL) followed by dichloromethane (15 mL) was added at 20-25° C. The reaction was stirred for 4 hours at the same temperature. After completion of the reaction, the reaction mixture was reduced to give brown oil (having an impurity of formula IIIa: 3.06 area-% HPLC).

The impurity of formula IIIa after purification of compound of formula IIa was measured by high performance liquid chromatography (HPLC) and the results are summarized herein below in Table-1.

TABLE-1

| | Purification of compound of formula IIa | | |
|---|---|---|---|
| Examples | Impurity of formula IIIa wt % (After amine deprotection step) | Impurity of formula IIIa wt % (After purification with an alkali metal perhalate) | Physical Nature |
| Example 1 (Step A) | 0.43 | 0.02 | Crystalline |
| Example 2 (Step A) | 0.29 | 0.04 | Crystalline |
| Reference Example 1 | 5.33 | Purification is not reported | Oily mass |
| Reference Example 2 | 3.06 | Purification is not reported | Oily mass |

The Following HPLC Method was Used: The HPLC system is equipped with a UV detector operating at 210 nm and an HPLC Column (YMC Pack Pro C18 RS (250×4.6) mm, 5 μm).

The Mobile Phases are:

Mobile Phase-A (MP-A): Add 2.72 g of potassium dihydrogen orthophosphate into a 2 L bottle. Add 2 L of HPLC grade water and 2 mL of triethylamine. Sonicate to dissolve the material completely. Adjust the pH of the solution to 3.2±0.03 with orthophosphoric acid.

Mobile Phase-B (MP-B): Acetonitrile.

The mobile phases are pumped through the column at a flow rate of (1.0 mL/min), column temperature of (25° C.) and auto sampler temperature of (5° C.).

The mixture of MP-A and MP-B was a gradient profile over the course of the (70 minutes) run as follows:

| Time (min.) | MP-A % | MP-B % |
|---|---|---|
| Initial | 65 | 35 |
| 40 | 35 | 65 |
| 50 | 25 | 75 |
| 59 | 25 | 75 |

| Time (min.) | MP-A % | MP-B % |
| --- | --- | --- |
| 60 | 65 | 35 |
| 70 | 65 | 35 |

It is evident from the comparative data of Table 1 that a high content of the diol impurity of formula IIIa is formed during the amine deprotection step, wherein the content of the diol impurity is even higher in prior art procedures of reference examples 1 and 2.

The invention claimed is:

1. A process for purifying a compound of formula II,

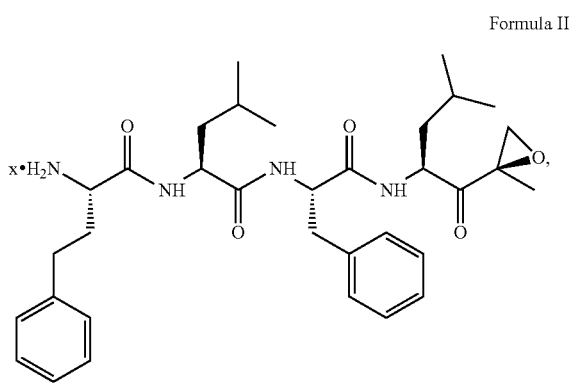

Formula II comprising an impurity of formula III:

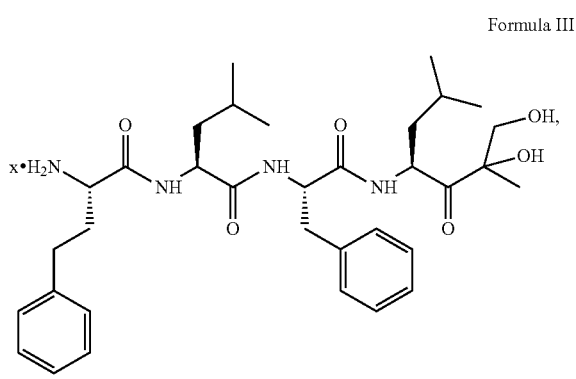

Formula III wherein X is independently trifluoroacetic acid, hydrochloric acid, hydrobromic acid, p-toluene sulfonic acid or phosphoric acid, the process comprising:
  a) treating the compound of formula II with an alkali metal perhalate in a solvent to reduce the amount of the impurity of Formula III in the compound of Formula II;
  b) adding an anti-solvent to precipitate the compound of formula II; and
  c) isolating a substantially pure compound of formula II.

2. The process according to claim 1, wherein the alkali metal perhalate is lithium periodate, sodium periodate, potassium periodate, lithium perbromate, sodium perbromate, potassium perbromate, lithium perchlorate, sodium perchlorate or potassium perchlorate.

3. The process according to claim 1, wherein the solvent is tetrahydrofuran, dioxane, dimethoxyethane, methanol, ethanol, propanol, isopropyl alcohol, n-butanol, ethyl acetate, acetonitrile, propionitrile, dimethylformamide, dimethylacetamide or dimethyl sulfoxide.

4. The process according to claim 1, wherein the anti-solvent is water, n-heptane, n-hexane, methyl tert-butyl ether or diisopropyl ether.

5. The process according to claim 1, wherein 'X' is trifluoroacetic acid.

6. The process according to claim 1, further comprising converting the substantially pure compound of formula II into carfilzomib of formula I,

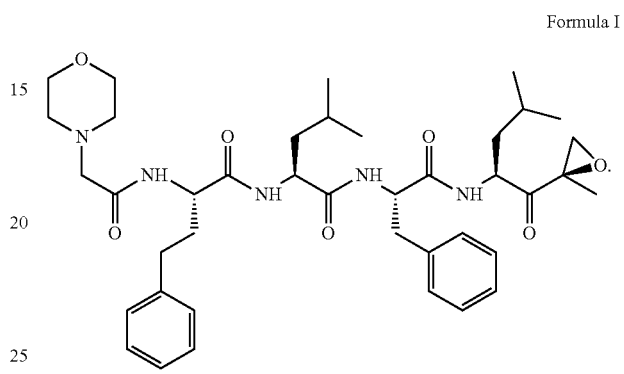

Formula I

7. The process according to claim 6, further comprising isolating the carfilzomib.

8. The process according to claim 7, wherein the isolated carfilzomib contains less than 0.15 area-% of diol carfilzomib impurity as measured by high performance liquid chromatography (HPLC).

9. The process of claim 1, comprising:
  i) treating the compound of formula II, wherein X is trifluoroacetic acid (Formula IIa), with an alkali metal perhalate comprising sodium periodate in a solvent comprising tetrahydrofuran, to reduce the amount of the impurity of Formula III in the compound of Formula II;
  ii) adding water as an anti-solvent to precipitate the compound of formula IIa; and
  iii) isolating substantially pure compound of formula IIa.

10. The process of claim 1, wherein:
  the alkali metal perhalate comprises lithium periodate, sodium periodate, potassium periodate, lithium perbromate, sodium perbromate, potassium perbromate, lithium perchlorate, sodium perchlorate or potassium perchlorate;
  the solvent comprises tetrahydrofuran, dioxane, dimethoxyethane, methanol, ethanol, propanol, isopropyl alcohol, n-butanol, ethyl acetate, acetonitrile, propionitrile, dimethylformamide, dimethylacetamide, or dimethyl sulfoxide; and
  the anti-solvent comprises water, n-heptane, n-hexane, methyl tert-butyl ether or diisopropyl ether.

11. The process of claim 7, wherein the carfilzomib comprises less than 0.15 area-% of the impurity of formula III as measured by high performance liquid chromatography (HPLC).

12. The process of claim 7, wherein the carfilzomib comprises less than 0.10 area-% of the impurity of formula III as measured by high performance liquid chromatography (HPLC).

13. The process of claim 7, wherein the carfilzomib comprises less than 0.05 area-% of the impurity of formula III as measured by high performance liquid chromatography (HPLC).

* * * * *